(12) United States Patent
Weiler (10) Patent No.: US 6,179,843 B1
(45) Date of Patent: Jan. 30, 2001

(54) DEVICE FOR INSERTION OF FOLDABLE INTRAOCULAR LENSES

(76) Inventor: Harold H. Weiler, P.O. Box 2078, Kilmarnock, VA (US) 22482

( * ) Notice: Under 35 U.S.C. 154(b), the term of this patent shall be extended for 0 days.

(21) Appl. No.: 08/896,302

(22) Filed: Jun. 28, 1997

(51) Int. Cl.$^7$ .................................................... A61F 9/00
(52) U.S. Cl. ............................................. 606/107; 623/6
(58) Field of Search ........................... 606/107; 128/898; 623/4, 6

(56) References Cited

U.S. PATENT DOCUMENTS

| | | |
|---|---|---|
| 4,681,102 | 7/1987 | Bartell . |
| 4,699,140 | 10/1987 | Holmes . |
| 4,822,360 | 4/1989 | Deacon . |
| 4,834,094 | 5/1989 | Patton . |
| 4,836,201 | 6/1989 | Patton . |
| 4,852,566 | 8/1989 | Callahan . |
| 4,919,130 * | 4/1990 | Stoy et al. ............................. 606/107 |
| 4,955,889 | 9/1990 | Van Gent . |
| 5,190,552 | 3/1993 | Kelman . |
| 5,304,182 | 4/1994 | Rheinish . |
| 5,354,333 | 10/1994 | Kammann . |
| 5,468,246 | 11/1995 | Blake . |
| 5,474,562 | 12/1995 | Orchowski . |
| 5,578,042 | 11/1996 | Cumming . |
| 5,582,613 | 12/1996 | Brady . |
| 5,582,614 | 12/1996 | Feingold . |
| 5,766,181 * | 6/1998 | Chambers et al. ................... 606/107 |

* cited by examiner

*Primary Examiner*—Glenn K. Dawson
(74) *Attorney, Agent, or Firm*—Kimberly A. Chasteen; John F. Carroll, IV

(57) ABSTRACT

A device for single-handed insertion of an intraocular lens into a patient's eye, having a barrel, a finger flange attached to the barrel, a plunger slidingly engaged with the barrel, a ring attached to the plunger, a projection extending from the plunger, along its length, for resisting bending in the plunger and transmission of torsion through the plunger and for assisting in preventing rotation of the plunger relative to the barrel, and a channel formed lengthwise along the interior of the barrel that engages the projection of the plunger. An alternative embodiment of the invention has a walled chamber, for receiving the lens, that forms an aperture to allow a trailing haptic of the lens to temporarily protrude outside the device. This embodiment can also include a rod for moving the lens through the chamber, with either the rod or the chamber having at least one groove along its length to allow the transmission of fluid through the device, away from the patient's eye, and for receiving the trailing haptic as the haptic is drawn from outside the device, through the aperture and into the chamber. The device is particularly adapted for insertion of acrylic-type lenses.

3 Claims, 3 Drawing Sheets

DEVICE FOR INSERTION OF FOLDABLE INTRAOCULAR LENSES

BACKGROUND

The present invention relates to an improved surgical device for single-handed insertion of various styles of foldable, intraocular lenses. The invention is a reusable device for compressing various styles of foldable, intraocular lenses; injecting these compressed lenses into patients' eyes in a controlled, single-handed fashion through extremely small incisions; and manipulating the lenses following injection. The invention is particularly useful in inserting acrylic-based lenses.

Many surgical procedures and devices have been developed during the fairly short history of cataract surgery. Prior to the introduction of foldable lenses, the state of the art of cataract lens replacement was performed by manual extra-capsular cataract extraction ("ECCE") and insertion of a rigid intraocular lens through a corneal or sclerocorneal incision that was typically 6.5 to 8.0 mm in length, or longer. The size of the wound created by such an incision typically required suturing. Patients who have undergone this form of cataract surgery experience complications such as endothelial cell loss, wound instability, postsurgical intraocular pressure rise, surgically induced astigmatism, and poor visual acuity during the postoperative period. The undesirable effects of ECCE and rigid lens implantation are largely attributable to wound size.

Since their introduction, elastic or "foldable," artificial lenses have become the replacement lens of preference for many cataract patients, particularly those undergoing phacoemulsification. Such a lens can be compressed and therefore occupies a smaller cross-sectional area than a rigid intraocular lens. Consequently, a foldable intraocular lens can be inserted through a smaller incision than a rigid lens. Implanting foldable lenses in this manner decreases wound size and contributes to earlier and better visual rehabilitation than large-incision surgery. Through phacoemulsification and injection of foldable intraocular lenses, the size of corneal and sclerocorneal incisions can be reduced by half or more. Instead of corneal or sclerocorneal incisions greater than 6.5 mm, cataract can be removed and intraocular lenses can be inserted through incisions of approximately 3.2 mm down to even 3.0 mm.

Although commercially available in several styles, foldable intraocular lenses generally share several characteristics. Foldable intraocular lenses are typically fabricated of materials that provide optical strength comparable to the natural lenses they replace, are chemically and biologically inert, and demonstrate durability characteristics that are necessary for articles permanently implanted in vivo. In addition, foldable intraocular lenses are elastic, capable of being compressed, passed through small incisions into the eye, and have resilience adequate to allow them to return to their intended shape following compression. The greater the resilience of a lens, the greater it can be compressed without permanent deformation, thereby allowing it to be inserted through relatively smaller incisions. Foldable intraocular lenses have traditionally been made of polymeric material such as silicone or polymethylmethacrylate ("PMMA"), but more recently, acrylic-based foldable intraocular lenses have become available.

Acrylic-based intraocular lenses are related to the PMMA rigid lenses in optical quality and chemistry. However, the nature of the material composition of acrylic-based lenses causes them to unfold slowly in the eye following insertion. This gives the surgeon much greater control during a most critical party of the surgery: insertion and manipulation of the lens within the capsular bag. Acrylic-based lenses have a "sticky" characteristic that causes adhesion of the lens to forceps, delaying the release of the lens into the capsular bag. Acrylic-based lenses are more fragile than silicone elastomer lenses. This can be demonstrated by examining lenses under a microscope after they have been grasped with forceps. Lens folding techniques that utilize forceps increase the risk of inducing lens surface defects and causing longitudinal cracks from taco-type folds. This is particularly true for those lenses that are of more fragile material composition than others, such as acrylic-based lenses. Consequently, there is a need for an inserter that can reduce the occurrence of surface scratches on fragile lens surfaces. Additionally, there is a need for an inserter that reduces the occurrence of central longitudinal cracks caused by taco-type folds.

In addition to material composition, foldable lenses differ structurally in the manner in which they are designed to be attached within the eye. There are three styles of lenses: one-piece, three-piece and hybrid lenses. A one-piece lens is manufactured entirely of optical quality material, with a refractive portion mounted in the center of an ovoid-rectangular plate that contains opposing fenestrations for attachment of the lens to the eye. Examples of one-piece lenses are the STAAR ELASTIC lens, model AA-4203VF and the STAAR TORIC lens, model AA-4203TF, both available from STAAR Surgical Company, Monrovia, Calif. U.S.A. Since one-piece lenses include integrated eye attachment points, one-piece lenses must be large enough to effectively fit the capsular bag of the eye.

Another style of intraocular lens is the three-piece lens. A three-piece lens is comprised of a central refractive portion made of optical quality material having, typically, two (2) haptics attached to its perimeter at opposite poles. The haptics are usually made of a shape-memory polymer, and are formed into a "C " or "J" shape. Examples of three-piece lenses are the STAAR ELASTIMIDE lens, mode AQ-1016V and the STAAR ELASTIMIDE lens, model AQ-2003V, both available from the STAAR Surgical Company, Monrovia, Calif. U.S.A.

A hybrid lens is also available. The hybrid lens combines the single-material construction of the one-piece lenses with the haptics found in three-piece lenses. Hybrid lenses are manufactured entirely of optical quality material, however, unlike one-piece lenses, they have a clearly defined central refractive portion from which haptics extend. Unlike three-piece lenses, the haptics of hybrid lenses are made of the same optical quality material as the plate of the one-piece lenses.

Lens selection is made by the surgeon based on the surgeon's personal preferences and the needs of a particular patient. Unfortunately, because many of the lens insertion tools presently on the market are designed for the insertion of only a particular size or style of lens, the choice of lens to be inserted often dictates the lens insertion tool used by the practitioner. Insertion devices for foldable intraocular lenses typically fall into three categories: forceps-type devices, screw-type devices and plunging-type devices. Forceps-type devices use opposable members to compress a foldable lens and insert the compressed lens through an incision in the eye. Screw-type and injector-type devices compress a foldable lens and then force it through a tube that has been placed in an incision in the eye. It is generally appreciated in the art that screw-type and injector-type devices provide an increased measure of compression and control over forceps-type devices and thereby reduce incision tearing while at the same time allowing for in vivo manipulation of the foldable lens.

Of the lens inserters presently available, the screw-type are most commonly used by practitioners. A screw-type inserter acts to compress and inject a lens by advancing a threaded plunger through a threaded tube. Examples of screw-type inserters are shown in Brady et al. U.S. Pat. Nos. 5,582,613, Patton et al. 4,834,094, Patton et al. 4,836,201, Kammann et al. 5,354,333, Blake 5,468,246, Orchowski et al. 5,474,562 and Feingold 5,582,614. Screw-type inserters are driven either electrically or manually. Electrically driven injectors are comprised of motors and gearings that are attendant to similar medical appliances. Such devices must be electrically isolated from the patient, must be specially designed to be sterilized, and by the nature of motor placement, typically have a large moment of inertia at the end of the device distal from the patient. This reduces the facility by which such devices may manipulate lenses following insertion. On the other hand, a manually actuated screw-type inserter requires a surgeon to provide both rotational actuation to the screw portion of the device and opposing resistance on the tube portion of the device to advance the screw within the tube and insert the lens into a patient's eye. Therefore, manually actuated screwtype injectors are, by the physics of their construction, two-handed devices.

Certain manually-actuated, plunging-type intraocular lens injectors are found in the prior art, and have been used to push compressed intraocular lenses through insertion tubes into patients' eyes. However, the unique challenges and physics associated with the eye place difficult demands on the devices and techniques employed by a surgeon performing ophthalmic surgery. As a result, the present state of the art should be improved to meet these demands and challenges.

Specifically, predictability in technique and device operation, even with the use of different sizes or styles of intraocular lenses, as well as affordability, is important to a successful surgical outcome. Consequently, there is a need for lens insertion devices that are reusable, easily sterilized, and cross-compatible with various types and styles of intraocular lenses, particularly acrylic-based lenses. Tactile and visual feedback is critical to an improved lens insertion device, as is ease of manipulation of the intraocular lens following its insertion into the eye. Therefore, there is a need for lens insertion devices that are lightweight and well balanced, that provide good hand control, that have a window so that the compression of lenses can be verified, that are constructed to certain tolerances to provide tactile feedback, and that have specially designed tips for maneuvering lenses following their insertion. Furthermore, there is a need for lens insertion devices that limit the insertion of foreign fluid, including air, into the eye. Importantly, there is also a need for a device that inserts an intraocular lens with a single-hand.

SUMMARY

A new device for inserting elastic intraocular lenses into patients' eyes has been invented encouraging predictability in surgical technique by providing certainty in device operation along with affordability. The device is reusable, easily sterilized, and cross-compatible with various types and styles of intraocular lenses, including acrylic-based lenses. The device provides tactile and visual feedback and easily manipulates an intraocular lens following insertion into the eye. The device is lightweight and well balanced, provides good hand control, has a window so that the compression of lenses can be verified, is constructed to specific tolerances to provide tactile feedback, and has a specially designed tips for maneuvering lenses following their insertion. Furthermore, the device limits the insertion of foreign fluid, including air, into the eye. Most importantly, the device allows the insertion of an intraocular lens with a single-hand.

In one broad aspect, the invention is directed to a device that has a walled chamber for receiving a lens. The wall of the chamber forms an aperture to allow a trailing haptic of the lens to temporarily protrude outside the device. The device has a rod for pushing the lens through the chamber and inserting the lens into the patient's eye. This rod has at least one groove along its length for allowing the transmission of fluid through the device, away from the patient's eye, and for receiving the trailing haptic as the haptic is drawn from outside the device, through the aperture and into the chamber. An alternative aspect of the same invention is directed to a device that has a walled chamber for receiving the lens, where the wall of the chamber forms an aperture to allow a trailing haptic of the lens to temporarily protrude outside the device. However, unlike the previously described embodiment, the chamber, not the rod, has at least one groove along its length to allow the transmission of fluid through the device, away from the patient's eye, and to receive the trailing haptic as the haptic is drawn from outside the device, through the aperture and into the chamber. Like the first embodiment, the device of the second embodiment also has a rod for pushing the lens through the chamber and inserting the lens into the patient's eye.

Another alternatively broad aspect of the invention is drawn to a device that has a walled chamber for receiving the lens, and also has a rod for moving the lens within the chamber. The rod has a tip for pushing the lens through the chamber and inserting the lens into the patient's eye. The tip of this rod has a concavity with surface areas for manipulating the lens translationally and rotationally within the eye following insertion. Each of these three aspects of the invention can have an insertion tube attached to the chamber, with a window formed in the insertion tube to allow a user of the device visual feedback regarding the state of compression of the lens or its haptics.

Another embodiment of the invention has a barrel with an attached finger flange for assisting a user in grasping the barrel with a hand. A plunger is slidingly engaged with the barrel, and a ring is attached to the plunger for assisting the user in grasping the plunger with the hand that contemporaneously grasps the barrel. This embodiment of the device has a projection extending from the plunger, along its length, for resisting bending and torsion in the plunger and for assisting in prevention of rotation of the plunger relative to the barrel, as well as a channel formed lengthwise along the interior of the barrel that engages the projection of the plunger for preventing rotation of the plunger relative to the barrel during sliding engagement of the plunger with the barrel.

An alternative embodiment of the invention has a barrel with an attached finger flange for assisting a user in grasping the barrel with a hand. This embodiment also has a plunger that is slidingly engaged with the barrel and has a ring attached to the plunger for assisting the user in grasping the plunger with the hand that contemporaneously grasps the barrel. However, unlike the previously described embodiment, this embodiment has a channel along the length of the plunger, and a projection extends lengthwise along the interior of the barrel. This projection engages the channel of the plunger and prevents rotation of the plunger relative to the barrel during sliding engagement of the plunger with the barrel.

More specifically, the walled chamber of each of these alternatives and embodiments can form an aperture that allows a trailing haptic of the lens to temporarily protrude outside the device. The chamber can also form an opening that is in communication with the aperture. A hinge can be attached to the chamber for rotation of a flap about: an open position, allowing the lens to be placed through the opening in the wall of the chamber into the device, and a closed position, prohibiting the lens from passing through the opening in the wall of the chamber. A flap can be attached to the hinge, and the flap can be maneuvered about the hinge and so that the opening in the wall of the chamber can be altered from the opened position to the closed position. A first tab can be attached to the second side of the chamber, extending radially from the chamber, for providing a surface upon which the device can be gripped by a user and for assisting in retaining the flap in the closed position. A second tab can be attached to the flap, extending radially from the chamber with the flap in the closed position, for providing a surface upon which the device can be gripped by a user and for assisting in retaining the flap in the closed position. A hollow retainer can be provided to slide into a retaining position over the device and retain the flap in the closed position. The retainer can be provided with a slot so that, with the flap in the closed position and the retainer slidingly engaged over the outer circumference of the chamber, the retainer can temporarily prohibit the rotation of the flap about the hinge, thereby retaining the flap in the closed position. The slot in the retainer receives the first tab and the second tab and prevents their relative movement when the retainer is placed in the retaining position. A dado can be formed in the retainer to accommodate the trailing haptic so that the haptic remains drawable into the device with the retainer in the retaining position.

Each of these alternatives and embodiments can be fabricated of surgical quality metal, such as titanium, of surgical quality polymer, or some combination thereof.

BRIEF DESCRIPTION OF THE DRAWINGS

A preferred embodiment of the present invention will be described in greater detail with reference to the accompanying drawings, wherein like elements bear like reference numerals and where.

DESCRIPTION

Figure 1:
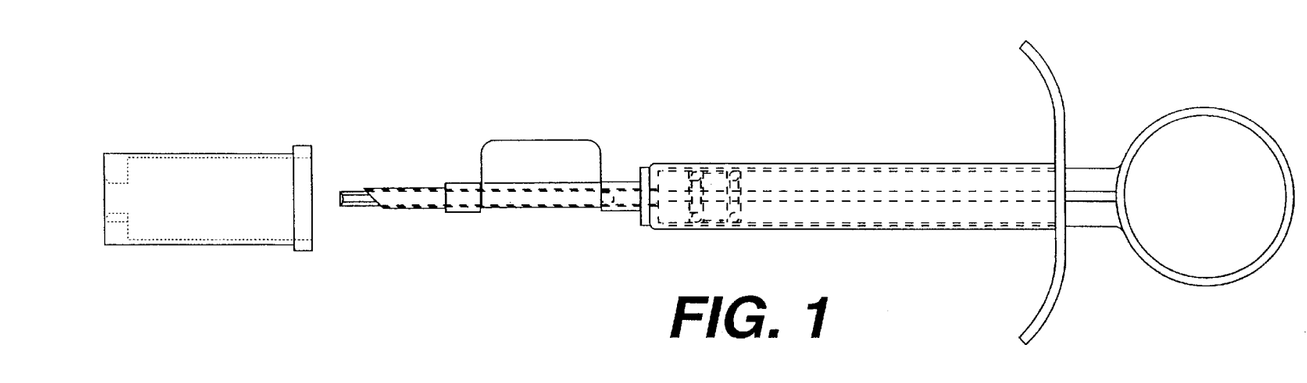
FIG. 1 shows an elevational view of an intraocular lens insertion device.
Figures 2, 2A:
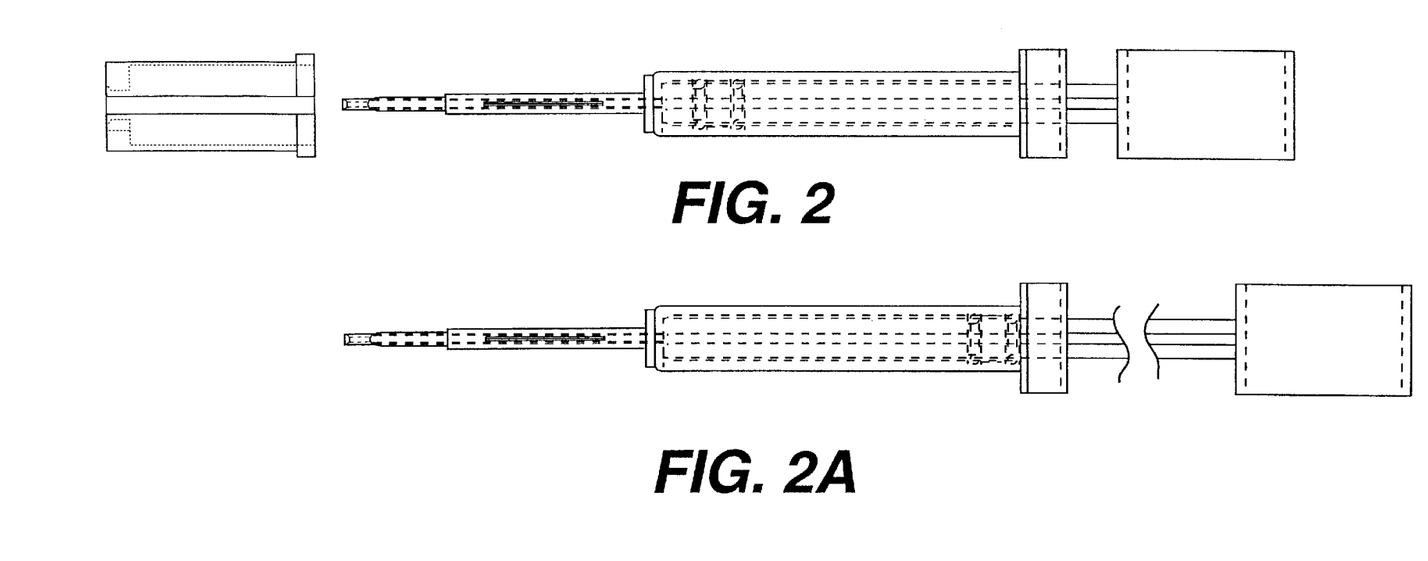
FIG. 2 shows a top view of the device of FIG. 1.
FIG. 2a shows the device of FIG.2 in the retracted position.
Figure 2B:
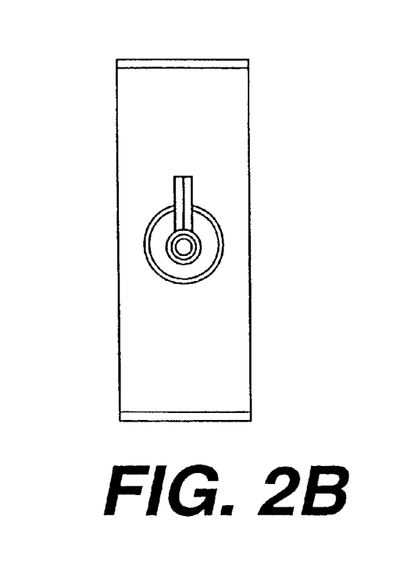
FIG. 2b shows and end view of the device of FIG. 2.
Figure 3:
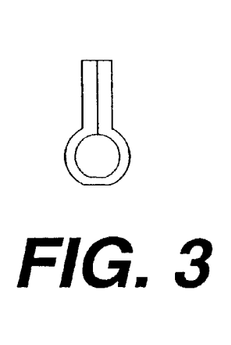
FIG. 3 shows a detail sectional view of the device of FIG. 1 taken along Section A—A.
Figure 8:
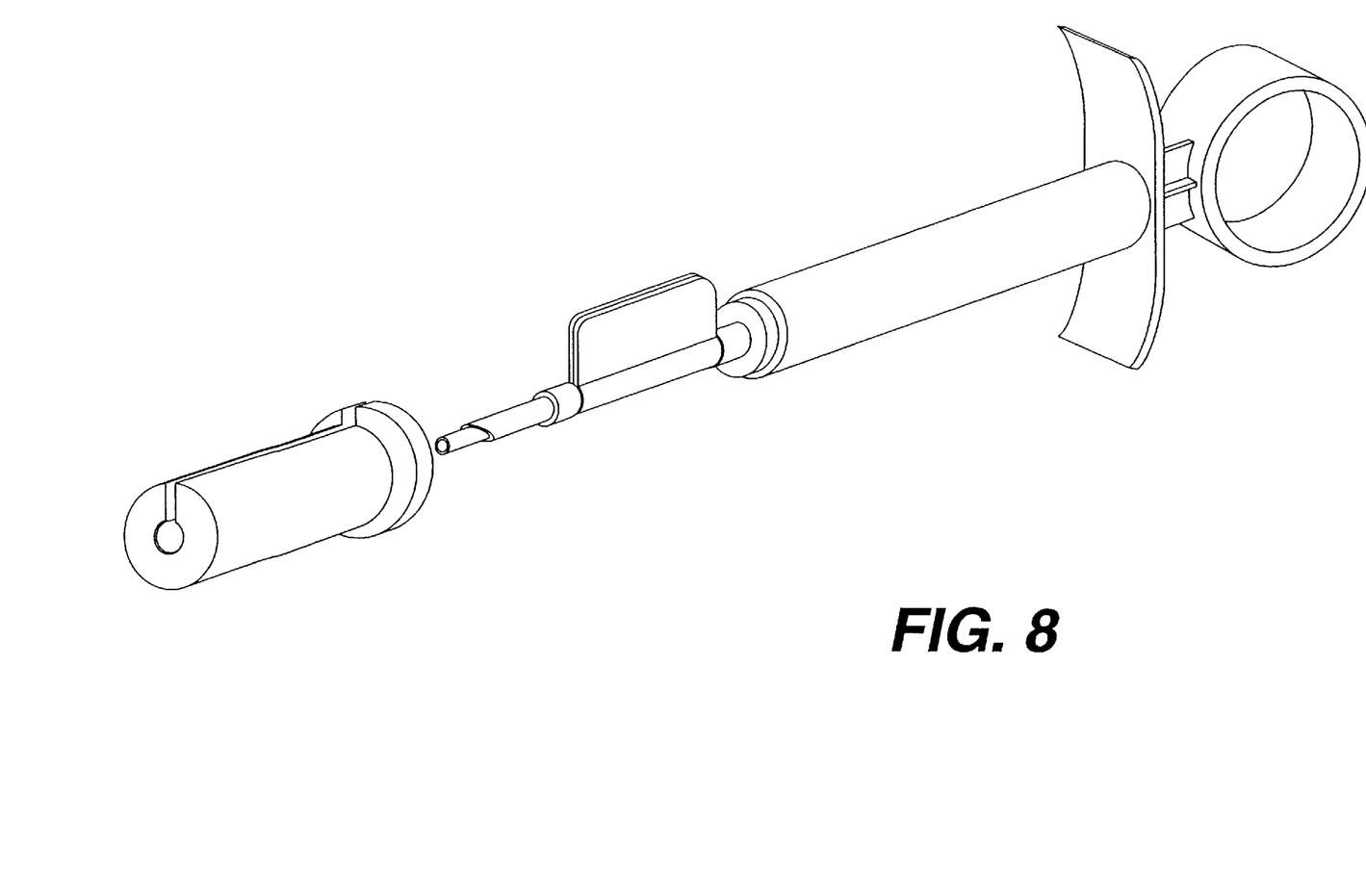
FIG. 8 is a perspective view of the device of FIG. 1.

With reference next to the drawings, FIGS. 1, 2 and 8 show a device 10 for inserting an intraocular lens into a patient's eye. The device 10 has a ring 12 of predominantly circular construction; however, a variety of shapes would suffice, so long as the function of the ring 12, as described herein, could still be performed. The ring 12 has an inner perimeter 14 that forms an opening 16. A user's thumb or other digit may pass through the opening 16 of the ring 12 so that actuating pressure may be placed upon the inner perimeter 14 of the ring 12. The ring 12 also has an outer perimeter 18. The device 10 has a plunger 20 with a first, posterior end 21 and a second, anterior end 23. The outer perimeter 18 of the ring 12 is attached to the posterior end 21 of the plunger 20. As actuating pressure is applied to the inner perimeter 14 of the ring 12, force is transferred through the attached plunger 20 and its constituent projections, or flanges 22, 24, 26, 28.

Figure 4:
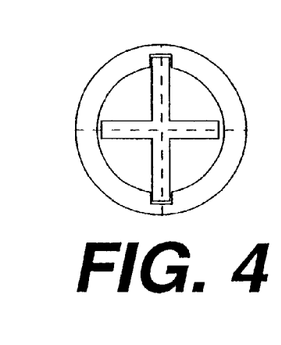
FIG. 4 shows a detail sectional view of the device of FIG. 1 taken along Section B—B.
Figure 5:
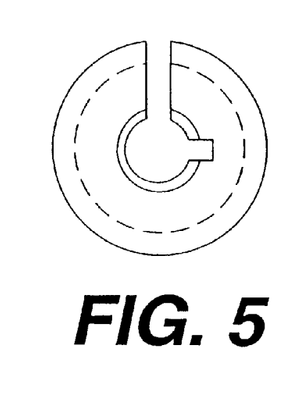
FIG. 5 shows a detail sectional view of the device of FIG. 1 taken along Section C—C.

As shown in FIG. 4, the flanges 22, 24, 26, 28 of the plunger 20 are set at right angles to each other. The flanges 22, 24, 26, 28 are placed in this manner to resist torque and bending stresses that result from the force transferred through the plunger 20. Although four (4) flanges 22, 24, 26, 28 are shown, less or more flanges would also be adequate to carry out the function herein described. Similarly, the flanges 22, 24, 26, 28 could be replaced with a tube or solid cylinder and still carry out the same function. The plunger 20 communicates within a hollow barrel 30 that has two (2) ends: a posterior end 32 being relatively closer to the ring 12 and a anterior end 34 being comparatively distal from the ring 12 of the device 10. The barrel 30 also has an external circumference 37.

As shown in FIG. 1, a finger flange 40 is attached to the posterior end 32 of the barrel 30. The finger flange 40 has one or more flange portions 42, 44. Preferably, the finger flange 40 has a first finger flange portion 42 and a second finger flange portion 44. The first finger flange portion 42 has a near part 46 that is attached to the posterior end 32 of the barrel 30. The first finger flange portion 42 also has a far part 48 that extends from the near part 46 of the first finger flange portion 42 and is curved at a radius r1 toward the anterior end 34 of the barrel 30. The second finger flange portion 44 has a near part 50 that is attached to the posterior end 32 of the barrel 30 opposite that of the first finger flange portion 42. The second finger flange portion 44 also has a far part 52 that extends from the near part 50 of the second finger flange portion 44 and is curved at a radius r2 toward the anterior end 34 of the barrel 30. The finger flange 40, the barrel 30 and the ring 12 can be provided with a textured surface or a gripable material to enhance the tactile response and feedback of the device 10.

As shown in FIG. 4, the barrel 30 has an outer surface 36 and an inner surface 38. The inner surface 38 forms at least one (1), but preferably two (2), parallel channels 54, 56 that run along the length of the inner surface 38 within the barrel 30. The two (2) channels include a top channel 54 and a bottom channel 56 that respectively can slidingly accommodate the top flange 22 and the bottom flange 24 of the plunger 20. This permits the actuation of the plunger 20 through the barrel 30 of the device 10 while limiting internal rotation of the plunger 20 relative to the barrel 30 and predominantly eliminating the internal transmission of torque via the plunger 20. The length of the barrel 30 should be adequate to accommodate the range of action of a rod 66 as described herein and as shown in FIGS. 2 and 2a.

Figure 6:
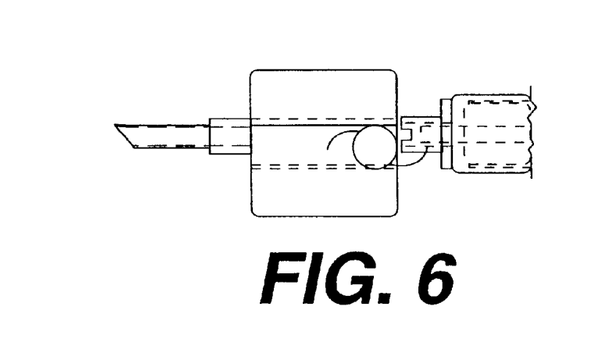
FIG. 6 is a partial elevational view of Detail "A" of the device of FIG. 1 showing the device in one mode of use.

As shown in FIG. 6, the device 10 has a chamber 58 for receiving an intraocular lens 91. The chamber 58 is formed predominantly by a wall 59 that encloses a hollow area defining an interior passageway 60. The chamber 58 has an exterior circumference 61, an anterior end 62 and a posterior end 64. The interior passageway 60 communicates between the anterior end 62 and the posterior end 64 of the chamber. The posterior end 64 of the chamber 58 is attached to the anterior end 34 of the barrel 30 so that the interior passageway 60 of the chamber 58 communicates with the hollow, inner surface 38 of the barrel 30 in which the plunger 20 travels. The rod 66 has an anterior end 67 and a posterior end 69. The posterior end 69 of the rod 66 is attached to the anterior end 23 of the plunger 20. Attachment between the rod 66 and the plunger 20 may be made by any one of a number of conventional methods, including by threads cut in the rod 66 that engage with threads tapped in the plunger 20; the attachment may also be made by welding, chemical adhesion; or, alternatively, the plunger 20 and the rod 66 may be formed from a single piece of material.

Figure 7A:
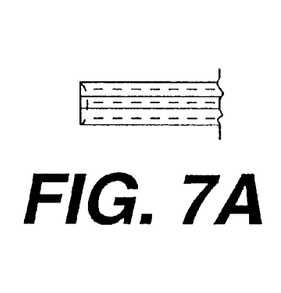
FIG. 7a is an elevational view of Detail "B" showing a portion of the rod of the device FIG. 1.
Figure 7B:
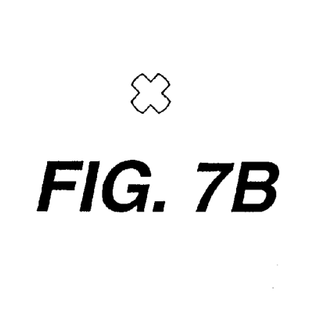
FIG. 7b is an end view of Detail "B" showing a portion of the rod of the device of FIG. 1.

As seen in FIGS. 1, 2 and 2a, the rod 66 is slidably contained within the interior passageway 60 of the chamber 58. As shown in FIGS. 7a and 7b, the rod 66 preferably forms one or more grooves 65 along its length. These grooves 65 are sized to permit fluid, such as saline solution, air, or ophthalmic lubricant, to pass between the rod 66 and the interior passageway 60 of the chamber 58 as the rod 66 slides within the interior passageway 60. This limits the accumulation of fluid pressure in the eye and reduces the amount of fluid transferred into a patient's eye. Preferably four (4) "V"-shaped grooves 65, with sidewalls of approximately sixty degrees (60°) are equally spaced around the rod 66. In an alternative embodiment, the rod 66 may be smooth and grooves may be formed by the interior passageway 60 of the chamber 58 to permit the passage of such fluid.

As shown in FIG. 6, approximately at a point centered along the length of the chamber 58, the wall 59 of the chamber 58 forms an opening covered by a flap 68. The flap 68 has a sidewall 76 with a first, ventral side 82 and a second, dorsal side 84. The flap 68 is attached to the chamber 58 by means of a hinge 74 located at the ventral portion 82 of the sidewall 76. The hinge 74 may be a true rotational attachment between the flap 68 and the chamber 58 should the flap 68 and the chamber 58 be separate articles. Preferably, however, the hinge 74 is a bendable connection between two (2) portions of the same article that form the chamber 58 and the flap 68. By rotation, or bending, as the case may be, of the flap 68 and the chamber 58 about the hinge 74, the flap 68 has an opened position 70 that allows communication between the passageway 60 of the chamber 58 and exterior of the device 10. Similarly, by rotation or bending of the flap 68 and the chamber 58 about the hinge 74, the flap 68 has a closed position 72 to prevent communication between the passageway 60 and exterior of the device 10.

The sidewall 76 of the flap 68 has an interior portion 78 and an exterior portion 80 formed such that the closed position 72 of the flap 68 causes the interior portion 78 of the sidewall 76 to be contiguous with the wall 59 of the passageway 60. A first tab 86 is attached to the wall 59 of the chamber 58 and extends radially therefrom. Attached to the dorsal portion 84 of the sidewall 76 of the flap 68 is a second tab 88. This second tab 88 extends radially from the chamber 58 with the flap 68 is in the closed position 72. When the flap 68 is in the closed position 72, the first tab 86 lies adjacent to, and in parallel planes with, the second tab 88. The first tab 86 and the second tab 88 perform several functions, including the following. They allow opposing forces to be placed on the chamber 58 to alter it from the closed position 72 to the open position 70 and vice versa. The tabs 86, 88 provide an area for the chamber 58 and flap 68 to be securely held in the closed position 72 by a retaining device. The tabs 86, 88 also provide a substantially planar gripping position for a user to manipulate the device 10.

Formed in the wall 59 of the chamber 58, preferably adjacent to that portion of the opening in the wall 59 that lies toward the posterior end 69 of the chamber 58, is a trailing haptic aperture 90 that is important for the operation of the device 10. As is shown in FIG. 6, and as has been discussed herein, three-part and hybrid intraocular lenses have haptics, also known colloquially as "hairs" or "whiskers." These tendril-like attachment members are used to connect intraocular lenses to patients' eyes. The haptics of an intraocular lens are formed in certain shapes that facilitate the insertion of the lens into the eye, the attachment of the lens within the eye, and the maintenance of the lens in the proper orientation within the eye. The importance of maintaining and protecting the structural integrity of haptics during intraocular lens injection cannot be understated; however, as intraocular insertion devices compress intraocular lenses, the haptics can easily become damaged. A crimped, crushed or otherwise permanently deformed haptic has a significantly deleterious impact on the ability of a surgeon to properly attach an intraocular lens in a patient's eye.

The device 10 employs several measures to reduce the likelihood of damage to haptics. One of these, as shown in FIGS. 1 and 6, is the provision of the trailing haptic aperture 90. This aperture 90 is offset along the wall 59 of the chamber 58 approximately ninety degrees (90°) from the position at which the first tab 86 is attached to the wall 59 of the chamber 58. The aperture 90 allows communication between the passageway 60 of the chamber 58 and an area immediately external of the device 10. As shown in FIG. 6, the flap 68 is placed in the opened position 70, and a three-piece or hybrid lens 91 is placed in the passageway 60. Three-piece and hybrid lenses 91 typically have two (2) haptics: a leading haptic 92 and a trailing haptic 94. The lens 91 is positioned in the passageway 60 so that the leading haptic 92 is directed toward the anterior end 62 of the chamber 58, and the trailing haptic 94 remains outside the chamber 58 until the flap 68 is placed in the closed position 72 and the rod 66 forces the lens 91 through the passageway 60 toward the anterior end 62 of the chamber 58, thereby drawing the trailing haptic 94 into the device 10.

When the flap 68 is placed in the closed position 72, thereby causing the lens 91 to be compressed and retained within the chamber 58, the leading haptic 92 is forced partially toward the anterior end 62 of the chamber 58. The trailing haptic 94 temporarily remains partially external of the device 10, lying in the aperture 90. The rod 66 then acts on the lens 91, and the lens 91 is forced down the passageway 60 toward the anterior end 62 of the chamber 58. The trailing haptic 94 then slides through the aperture 90 into the passageway 60 behind the lens 91. As the trailing haptic 94 slides into the passageway 60, the trailing haptic 94 is received by a groove 65 in the rod 66 (or by a groove in the wall 59 of the passageway 60, as the case may be). In addition to limiting the transfer of fluid into the eye, the groove 65 in the rod 66 also receives the trailing haptic 94, and prevents the haptic 94 from being crushed, damaged or otherwise deformed. The spacing between the rod 66 and the passageway 60 are proportionate to the diameter of a haptic, therefore, should the trailing haptic 94 fail to fall in the groove 65, the rod 66 will not be able to freely pass within the passageway 60, thereby giving the user of the device 10 tactile feedback regarding the status of the lens 91 and the haptics 92, 94.

The device 10 also has an insertion tube 96 with an anterior end 98 and a posterior end 100. The insertion tube 96 has a wall 102 that forms internal bore 106 that communicates between the anterior end 98 and the posterior end 100. The insertion tube 96 has an external circumference 104. The posterior end 100 of the insertion tube 96 is attached to the anterior end 62 of the chamber 58 so that the internal bore 106 communicates with the passageway 60 of the chamber 58. The insertion tube 96 can be attached to the chamber 58 by any one of a number of methods, including interference fit between the external circumference 104 of the insertion tube 96 and a counterbore 97 in the anterior end 62 of the chamber 58. Also, the chamber 58 and the insertion tube 96 may be joined by welding, interlocking threads or chemical adhesion. Additionally, the insertion tube 96 and the chamber 58 may be formed of a single piece of material.

The wall 102 of the insertion tube 96 forms a window 108 that communicates between the internal bore 106 of the insertion tube 96 and outside the device 10. The window 108 provides visual feedback to a user as to the status of the lens 91 and the haptics 92, 94 as they pass through the internal bore 106 of the insertion tube 96. The window 108 passes entirely through the wall 102 of the insertion tube 96. The window 108 can be ovoid in shape. The window 108 may be filled with transparent, surgical quality material, such as quartz, or, preferably, it may be left unfilled.

The anterior end 98 and external circumference 104 of the insertion tube 96 are designed to prevent incision tearing or inelastic incision deformation. The anterior end 98 of the insertion tube 96 is preferably terminated perpendicular to the length of the insertion tube 96 to facilitate lens 91 decompression following injection into a patient's eye, although terminating the anterior end 98 at an angle is possible and may also facilitate lens 91 decompression for certain styles of lenses. The external circumference 104 of the insertion tube 96 is smooth and sized to be inserted into and removed from a patient's eye with either no distortion of the incisional tissue, or without undue inelastic incision deformation or tearing of incisions. Such incisions are typically on the order of 2.5 mm to 3.5 mm, but preferably from about 2.8 mm to 3.0 mm, and most preferably 2.8 mm.

As shown in FIGS. 1, 2, 7a and 7b, the rod 66 of the device 10 has a tip 110 that specially facilitates manipulation of the lens 91 after the rod 66 is inserted in a patient's eye. The rod tip 110 has a center portion 114 and a perimeter portion 112 that runs around the circumference of the rod tip 110 and a center portion 114. The rod tip 110 forms a shallow concavity so that the center portion 114 is slightly posterior the perimeter portion 112 of the tip 110 thereby forming a tip surface 111. After the lens 91 travels through the passageway 60 of the chamber 58 and through the internal bore 106 of the insertion tube 96, the lens 91 passes the anterior end 98 of the insertion tube 96 and is injected into a patient's eye. The rod tip 110, then protruding from the anterior end 98 of the insertion tube 96, can manipulate the lens 91 within the patient's eye. The tip surface 111 can be used to translate the lens 91 within the patent's eye, and the tip perimeter 112 can be used to rotate the lens 91.

The device 10 also has a retainer 116. The retainer 116 has a wall 118 that forms a substantially hollow, right circular cylinder with an interior portion 120, an exterior portion 121, an anterior portion 122 and a posterior portion 124. The interior portion 120 of the retainer 116 has a large bore 126, a small bore 128 and a countersunk portion 130. The large bore 126 of the retainer 116 is dimensioned to accommodate the external circumference 37 of the barrel 30 of the device 10. The small bore 128 of the retainer 116 is dimensioned to accommodate the external circumference 61 of the chamber 58. The wall 118 of the retainer 116 is segmented by a slot 132 that runs along its length for purposes specified herein. Approximately ninety degrees (90°) along the interior 120 of the retainer 116, a dado 134 is provided in the wall 118 of the retainer 116 for purposes specified herein. The exterior 121 is provided with a lip 136 at the posterior 124 of the retainer 116 to facilitate manipulation of the retainer 116.

As shown in FIG. 1, starting from a protruded position 140, the device 10 is placed in a retracted position 138 by placement of a user's thumb or other digit through the opening 16 or along the outer perimeter 18 of the ring 12 and the user also grasping the finger flange 40 or the barrel 30 of the device 10. With the same hand, opposing pressure can then placed between the ring 12 and the other portion of the device 10 to which the user is applying pressure, whether that be the barrel 30 or the finger flange 40. The ring 12 is therefore drawn away from the finger flange 40 and the barrel 30, thereby drawing the plunger 20, to which the ring 12 is attached, along with it, through the barrel 30 and past the finger flange 40. As the plunger 20 is drawn through the barrel 30, the flanges 22, 24, 26, 28 inhibit bending in the plunger 20. The top flange 22 and the bottom flange 24, being engaged in top channel 54 and the bottom channel 56, respectively, of the barrel 30, prevent the ring 12 and the plunger 20 from rotating within the barrel 30.

The rod 66, being attached to the plunger 20, is drawn through the internal bore 106 of the insertion tube 96 and through the passageway 60 of the chamber 58, into the barrel 30 until the tip 110 of the rod 66 has been drawn past the haptic aperture 90. The retainer 116 can then be placed on the insertion tube 96 and barrel 30 of the device, beginning by placing the anterior end 98 of the insertion tube 96 through the large bore 126 of the retainer 116, at the posterior end 124 of the retainer, and moving the retainer 116 toward the posterior end 100 of the insertion tube 96, the anterior end 62 of the chamber 58, the posterior end 64 of the chamber 58, and then the anterior end 34 of the barrel 30. In this process, the first tab 86 and the second tab 88 pass through the slot 132 of the retainer 116, and the small bore 128 of the retainer 116 passes over the anterior end 98 of the insertion tube 96, the posterior end 100 of the insertion tube 96, the anterior end 62 of the chamber 58 and the posterior end 64 of the chamber 58, so that the anterior end 122 of the retainer 116 is posterior to the trailing haptic aperture 90.

After being placed in the above-described retracted position 138, the device 10 can be readied to insert an intraocular lens 91 into a patient's eye. Assuming the flap 68 is in the closed position 72, the first tab 86 can be grasped as well as the second tab 88, the ring 12, barrel 30 or finger flange 40, and opposing pressure placed therebetween so as to rotate the flap 68 around the hinge 74 until the flap 68 is in the open position 70. An intraocular lens 91 can then be placed in the passageway 60 of the chamber 58. If the lens 91 is a single-piece lens, the ovoid-rectangular plate is placed longitudinally along the length of the passageway 60. The opposing fenestrations of the lens are situated within the passageway 60 so that one fenestration is toward the anterior end 62 of the chamber 58 and the other fenestration is positioned toward the posterior end 64 of the chamber 58. If the lens 91 is a three-piece lens or a hybrid lens, the lens 91 is placed in the passageway 60 of the chamber 58 so that the leading haptic 92 is toward the anterior end 62 of the chamber 58. The trailing haptic 94 is positioned toward the posterior end 64 of the chamber 58. The first tab 86 is grasped along with the second tab 88, the ring 12, barrel 30 or finger flange 40, and pressure placed therebetween so as to rotate the flap 68 around the hinge 74 until the flap 68 is in the closed position 72 and the first tab 86 and the second tab 88 are contiguous. By moving the flap 68 into the closed position 72, as described herein, and placing the first tab 86 contiguous to the second tab 88, the trailing haptic 94 can pass through the trailing haptic aperture 90, and, temporarily, be external of the device 10. The retainer 116 can then be moved anteriorly so that the contiguous first tab 86 and second tab 88 partially pass through the slot 132 of the retainer 116, and the trailing haptic 94 can lie within the dado 134 of the retainer 116.

The device 10, readied for insertion of an intraocular lens in this manner, causes the lens 91 to be rolled in a tubular configuration for insertion thereby preventing abrupt folds (e.g., a taco configuration) that other inserters such as forceps typically induce. Such folds are undesirable because they cause cracks and/or creases in lenses. Additionally, folding with forceps can damage surface integrity of lenses, particularly of fragile lenses such as acrylic-based lenses. The device 10 is specifically beneficial for the insertion of an acrylic intraocular lenses as the tubular rolling allows continuous control and slow insertion with positive placement of the lens 91 within the capsular bag. Additionally, the tubular rolling causes the sticky material composition of the lens 91 to be less likely to adhere to the device 10 than to forceps. Also, tubular rolling of the lens 91 reduces the incidence of lens cracking when compared with lenses grasped with forceps and folded in a taco fashion.

Having readied the device 10 for insertion of an intraocular lens, the insertion tube 96 of the device 10 can then be placed though an incision in a patient's eye, and the lens can be injected therethrough. This is performed by a user of the device 10 first placing the lens 91 in position for injection by placing a thumb or other digit through the ring 12 of the device 10 and grasping, with the same hand, if so desired, the first finger flange portion 42, the second finger flange portion 44, and/or the barrel 30 of the device, and drawing the ring 12 toward the finger flange 40. This action forces the plunger 20, which is attached to the ring 12 through the barrel 30. The flanges 22, 24, 26, 28 prevent the plunger 20 from bending, and the top flange 22 and bottom flange 24 engage in the top channel 54 and bottom channel 56 of the inner surface 38 of the barrel 30 and prevent the plunger 20 from rotating within the barrel 30. The movement of the plunger 20 acts to move the rod 66 through the barrel 30, the passageway 60 of the chamber 58, and through the insertion tube 96, until the rod tip 110 and the anterior end 67 of the rod 66 protrude from the anterior end 98 of the insertion tube 96.

When the rod 66 travels through the passageway 60 of the chamber 58 and the internal bore 106 of the insertion tube 96 from a posterior position in the device 10 to an anterior position, the rod tip 110 impinges upon the lens 91, compressing it and forcing it through the passageway 60 of the chamber 58 and through the internal bore 106 of the insertion tube 96 until the lens 91 passes through the anterior end 98 of the insertion tube 96. Prior to the lens 91 being expelled from the device 10, the insertion tube 96 is placed into a patient's eye and the lens 91 is forced through the anterior end 98 of the insertion tube 96, into a patient's eye.

As the lens 91 is traveling through the passageway 60 and the internal bore 106 of the insertion tube 96, the leading haptic 92 is forced along ahead of the lens 91, and the trailing haptic 94 passes through a channel formed by the dado 134 of the retainer 116 and the wall 59 of the chamber 58, through the trailing haptic aperture 90, into the passageway 60 of the chamber 58, and is retained in a groove 65. This protects the trailing haptic 94 from unwanted deformation. Preferably, the tolerances of the passageway 60, the internal bore 106 of the insertion tube 96, and the trailing haptic 94 are such that should the trailing haptic be deformed by the action of the rod 66 within the passageway 60 or within the internal bore 106 of the insertion tube 96, frictional tactile feedback will be given to the user and the lens 91 can be readjusted or removed and replaced prior to insertion into a patient's eye.

As the rod 66 passes through the passageway 60 and the internal bore 106 of the insertion tube 96, the grooves 65 allow the migration of fluid, such as saline, ophthalmic lubricant and air, away from an area of higher pressure, anterior of the tip 110, to an area of lower pressure, posterior of the tip 110. This reduces the amount of such fluid injected into a patient's eye. In addition, the window 108 in the insertion tube 96 of the device 10 provides a user with visual feedback regarding the quality of the lens 91 compression caused by the tip 110. The window 108 allows visual inspection of the compressed lens 91 prior to it being injected in a patient's eye. The window 108 assists the user in determining if the lens 91 is improperly compressed, or if the haptics 92, 94 have been damaged by the compression process. If so, the lens 91 can be removed from the device 10 and reinserted or replaced prior to insertion into a patient's eye. Following injection of the lens 91 in a patient's eye, the tip surface 111, the perimeter of the rod tip 112 and the center portion 114 of the rod tip 110 can be used to manipulate the lens 91 into position for suturing.

It should be understood that the described embodiments merely illustrate principles of the invention in preferred forms. Many modifications, additions and deletions may be made without departure from the description provided. For example, although the device 10 is intended to be constructed entirely of surgical grade metal such as stainless steel or titanium, it may also be constructed of polymeric material that is disposable. Additionally, the device could be manufactured of polymeric or composite material that is able to be sterilized and reused. Furthermore, certain portions of the device, for example, those portions that interact directly with the lens 91, could be made of disposable polymeric material while others can be made of metallic, or other nondisposable material. It thus is seen that a reusable device for compressing various styles of foldable, intraocular lenses, insertion these compressed lenses into patients'eyes in a controlled, single-handed fashion through extremely small incisions, and manipulating the lenses following insertion can be made.

What is claimed is:

1. A device for single-handed insertion of an intraocular lens into a patient's eye, comprising:

(a) a barrel having a hollow interior, an anterior end and a posterior end;

(b) a finger flange attached to the posterior end of the barrel for assisting a user in grasping the barrel with a hand;

(c) a plunger having an anterior end and a posterior end, the anterior end of the plunger slidingly engaged with the posterior end of the barrel;

(d) a ring attached to the posterior end of the plunger for assisting the user in grasping the plunger with the hand that contemporaneously grasps the barrel;

(e) a projection extending from the plunger, along its length, for resisting bending in the plunger and transmission of torsion through the plunger and for assisting in preventing rotation of the plunger relative to the barrel;

(f) a channel formed lengthwise along the interior of the barrel that engages the projection of the plunger for preventing rotation of the plunger relative to the barrel during sliding engagement of the plunger with the barrel;

(g) a walled chamber for receiving the lens, the chamber having an outer circumference, an anterior portion and a posterior portion, the wall of the chamber forming an aperture to allow a trailing haptic of the lens to temporarily protrude outside the device, said chamber also forming an opening with a first side and a second side, the opening and the aperture being in communication with each other, the posterior end of the chamber attached to the anterior end of the barrel;

(h) a hinge attached to the first side of the chamber for rotation of a flap about an open position, allowing the lens to be placed through the opening in the wall of the chamber into the device, and a closed position, prohibiting the lens from passing through the opening in the wall of the chamber;

(i) a flap having a first edge and a second edge, the first edge of the flap being attached to the hinge so that the flap can be maneuvered about the hinge and so that the opening in the wall of the chamber can be altered from the opened position to the closed position;

(j) a first tab attached to the second side of the chamber, the first tab extending radially from the chamber, the first tab for providing a surface upon which the device can be gripped by a user and for assisting in retaining the flap in the closed position;

(k) a second tab attached to the second edge of the flap, the second tab extending radially from the chamber with the flap in the closed position, the second tab for providing a surface upon which the device can be gripped by a user and for assisting in retaining the flap in the closed position;

(l) a walled insertion tube having an internal bore and a posterior end, the posterior end of the insertion tube being attached to the anterior end of the chamber so that the internal bore of the insertion tube is in communication with the chamber, the insertion tube for transmission of the lens from the chamber, through the internal bore and into the patient's eye, and the wall of the insertion tube forming a window to allow a user visual feedback regarding deformation of the lens and transmission of the haptic within the device prior to insertion of the lens into the patient's eye;

(m) a rod attached to the anterior end of the plunger for:
  (i) pushing the lens through the chamber,
  (ii) receiving a trailing haptic of the lens,
  (iii) pushing the lens through the insertion tube,
  (iv) inserting the lens into the patient's eye, and
  (v) allowing the transmission of fluid through the device, away from a patient's eye;

(n) said rod having:
  (i) at least one groove along its length for allowing the transmission of fluid through the device, away from the patient's eye and for receiving the trailing haptic as the haptic is drawn from outside the device, through the aperture and into the chamber, and
  (ii) a tip for pushing the lens through the chamber and through the insertion tube and inserting the lens into the patient's eye, the tip of said rod having a concavity with surface areas on the tip for manipulating the lens translationally and rotationally within the eye following insertion; and (o) a hollow retainer with an inner circumference to accommodate the outer circumference of the chamber and a slot, the inner circumference being slidably engageable into a retaining position over the outer circumference of the chamber so that with the flap in the closed position and the inner circumference of the retainer slidingly engaged over the outer circumference of the chamber, the retainer temporarily prohibits the rotation of the flap about the hinge, thereby retaining the flap in the closed position, the slot for receiving the first tab and the second tab and preventing their relative movement when the retainer is placed in the retaining position, the inner circumference of the retainer forming a dado to accommodate the trailing haptic drawable into the device with the retainer in the retaining position.

2. The intraocular lens insertion device of claim 1 wherein the device is fabricated of titanium.

3. A device for single-handed insertion of an acrylic-type intraocular lens into a patient's eye, comprising:

(a) a barrel having a hollow interior, an anterior end and a posterior end;

(b) a finger flange attached to the posterior end of the barrel for assisting a user in grasping the barrel with a hand;

(c) a plunger having an anterior end and a posterior end, the anterior end of the plunger slidingly engaged with the posterior end of the barrel;

(f) a ring attached to the posterior end of the plunger for assisting the user in grasping the plunger with the hand that contemporaneously grasps the barrel;

(g) a projection extending from the plunger, along its length, for resisting bending in the plunger and transmission of torsion through the plunger and for assisting in preventing rotation of the plunger relative to the barrel;

(f) a channel formed lengthwise along the interior of the barrel that engages the projection of the plunger for preventing rotation of the plunger relative to the barrel during sliding engagement of the plunger with the barrel;

(g) a walled chamber for receiving the lens, the chamber having an outer circumference, an anterior portion and a posterior portion, the wall of the chamber forming an aperture to allow a trailing haptic of the lens to temporarily protrude outside the device, said chamber also forming an opening with a first side and a second side, the opening and the aperture being in communication with each other, the posterior end of the chamber attached to the anterior end of the barrel;

(h) a hinge attached to the first side of the chamber for rotation of a flap about an open position, allowing the lens to be placed through the opening in the wall of the chamber into the device, and a closed position, prohibiting the lens from passing through the opening in the wall of the chamber;

(i) a flap having a first edge and a second edge, the first edge of the flap being attached to the hinge so that the flap can be maneuvered about the hinge and so that the opening in the wall of the chamber can be altered from the opened position to the closed position;

(j) a first tab attached to the second side of the chamber, the first tab extending radially from the chamber, the first tab for providing a surface upon which the device can be gripped by a user and for assisting in retaining the flap in the closed position;

(k) a second tab attached to the second edge of the flap, the second tab extending radially from the chamber with the flap in the closed position, the second tab for providing a surface upon which the device can be gripped by a user and for assisting in retaining the flap in the closed position;

(l) a walled insertion tube having an internal bore and a posterior end, the posterior end of the insertion tube being attached to the anterior end of the chamber so that the internal bore of the insertion tube is in communication with the chamber, the insertion tube for transmission of the lens from the chamber, through the internal bore and into the patient's eye, and the wall of the insertion tube forming a window to allow a user visual feedback regarding deformation of the lens and transmission of the haptic within the device prior to insertion of the lens into the patient's eye;

(m) a rod attached to the anterior end of the plunger for:
  (i) pushing the lens through the chamber,
  (ii) receiving a trailing haptic of the lens,
  (iii) pushing the lens through the insertion tube,
  (iv) inserting the lens into the patient's eye, and
  (v) allowing the transmission of fluid through the device, away from a patient's eye;

(n) said rod having:
  (i) at least one groove along its length for allowing the transmission of fluid through the device, away from the patient's eye and for receiving the trailing haptic as the haptic is drawn from outside the device, through the aperture and into the chamber, and
  (ii) a tip for pushing the lens through the chamber and through the insertion tube and inserting the lens into the patient's eye, the tip of said rod having a concavity with surface areas on the tip for manipulating the lens translationally and rotationally within the eye following insertion; and (o) a hollow retainer with an inner circumference to accommodate the outer circumference of the chamber and a slot, the inner circumference being slidably engageable into a retaining position over the outer circumference of the chamber so that with the flap in the closed position and the inner circumference of the retainer slidingly engaged over the outer circumference of the chamber, the retainer temporarily prohibits the rotation of the flap about the hinge, thereby retaining the flap in the closed position, the slot for receiving the first tab and the second tab and preventing their relative movement when the retainer is placed in the retaining position, the inner circumference of the retainer forming a dado to accommodate the trailing haptic drawable into the device with the retainer in the retaining position.

\* \* \* \* \*